US012699091B2

(12) United States Patent
Grinbergs Salas et al.

(10) Patent No.: US 12,699,091 B2
(45) Date of Patent: Aug. 4, 2026

(54) **METHOD AND KIT FOR DETECTING THE PRESENCE OF SILVER LEAF DISEASE *CHONDROSTEREUM PURPUREUM* FUNGUS**

(71) Applicant: INSTITUTO DE INVESTIGACIONES AGROPECUARIAS, Providencia (CL)

(72) Inventors: Daina Grinbergs Salas, Providencia (CL); Ricardo Javier Chilian, Providencia (CL); Jaime Humberto Mejias Bassaletti, Providencia (CL); René Andrés France Iglesias, Providencia (CL)

(73) Assignee: INSTITUTO DE INVESTIGACIONES AGROPECUARIAS, Providencia (CL)

( * ) Notice: Subject to any disclaimer, the term of this patent is extended or adjusted under 35 U.S.C. 154(b) by 293 days.

(21) Appl. No.: 18/229,533

(22) Filed: Aug. 2, 2023

(65) Prior Publication Data

US 2024/0183853 A1     Jun. 6, 2024

Related U.S. Application Data

(60) Provisional application No. 63/394,495, filed on Aug. 2, 2022.

(51) Int. Cl.
| | |
|---|---|
| *C07K 16/00* | (2006.01) |
| *C07K 16/14* | (2006.01) |
| *G01N 33/543* | (2006.01) |
| *G01N 33/553* | (2006.01) |
| *G01N 33/569* | (2006.01) |

(52) U.S. Cl.
CPC ....... *G01N 33/56961* (2013.01); *C07K 16/14* (2013.01); *G01N 33/54346* (2013.01); *G01N 33/553* (2013.01); *G01N 2333/37* (2013.01); *G01N 2469/10* (2013.01)

(58) Field of Classification Search
CPC combination set(s) only.
See application file for complete search history.

(56) References Cited

U.S. PATENT DOCUMENTS

| | | |
|---|---|---|
| 5,563,040 A | 10/1996 | Clausen et al. |
| 2016/0273055 A1 | 9/2016 | Mills et al. |
| 2016/0299136 A1 | 10/2016 | Ozalp et al. |
| 2020/0299752 A1 | 9/2020 | Stephens |

FOREIGN PATENT DOCUMENTS

| | | |
|---|---|---|
| CN | 110806481 | 2/2020 |
| WO | WO2014174085 | 10/2014 |
| WO | WO2016035099 | 3/2016 |
| WO | WO2017037408 | 3/2017 |
| WO | WO2018097796 A1 | 5/2018 |

OTHER PUBLICATIONS

Mejias et al (International Congress of Plant Pathology (ICPP) 2018. Conference: International Congress of Plant Pathology (ICPP) 2018: Plant Health in a Global Economy at: Boston, Massachusetts, U.S.A) ; abstract only at this time.*
Senda et al (Journal of General Plant Pathology (2001), 67(1),41-44).*
Cruz et al (Red Agricola. 2021., ppl. 1-13; web version); [ note: not presently translated. Cited in Applicants' related WO2024.026578 PCT/CL2023/050067].*

* cited by examiner

*Primary Examiner* — Jennifer E Graser
(74) *Attorney, Agent, or Firm* — MUNCY, GEISSLER, OLDS & LOWE, P.C.

(57)     ABSTRACT

An antibody that is used to detect the presence of the *Chondrostereum purpureum* fungus in a plant sample, where the antibody specifically binds to the endolipogalacturonase enzyme produced by *Chondrostereum purpureum* (anti-endoPG from now). A kit and a method to detect fungal antigens, particularly, to detect the presence of the silverleaf disease (caused by the *Chondrostereum purpureum* fungus) in fruit trees, by means of detection of the endoPG enzyme through the binding of said antigen to the antibody, functionalized with gold nanoparticles, where the binding is detected via enzyme-linked immunosorbent assays (ELISA) or an immunochromatographic lateral flow assay.

10 Claims, 11 Drawing Sheets

Specification includes a Sequence Listing.

SEQUENCE LISTING

```
Sequence total quantity: 4
SEQ ID NO: 1          moltype = DNA  length = 1434
FEATURE               Location/Qualifiers
source                1..1434
                      mol_type = other DNA
                      organism = synthetic construct
SEQUENCE: 1
atggaatgta actggatact tccttttatt ctgtcagtaa cttcaggtgt ctactcacag  60
gttcagctcc agcagtctgg ggctgagctg gcaagacctg gggcttcagt gaagttgtcc  120
tgcaaggctt ctggctacac ctttactagc tactggatgc agtgggtaaa acagaggcct  180
ggacagggtc tggaatggat tggggctatt tatcctggag atggtgatac taggtacact  240
cagaagttca agggcaaggc cacattgact gcagataaat cctccagcac agcctacata  300
caactcagca gcttggcatc tgaggactct gcggtctatt actgtgcaag attcccgncg  360
gatggttctt attcctatgc tatggactac tggggtcaag gaacctcagt caccgtctcc  420
tcagccaaaa caacacccce atcagtctat ccactggccc ctgggtgtgg agatacaact  480
ggttcctccg tgactctggg atgcctggtc aagggctact tccctgagtc agtgactgtg  540
acttggaact ctggatccct gtccagcagt gtgcacacct tcccagctct cctgcagtct  600
ggactctaca ctatgagcag ctcagtgact gtcccctcca gcacctggcc aagtcagacc  660
```

-continued

```
gtcacctgca gcgttgctca cccagccagc agcaccacgg tggacaaaaa acttgagccc   720
agcgggccca tttcaacaat caacccctgt cctccatgca aggagtgtca caaatgccca   780
gctcctaacc tcgagggtgg accatccgtc ttcatcttcc ctccaaatat caaggatgta   840
ctcatgatct ccctgacacc caaggtcacg tgtgtggtgg tggatgtgag cgaggatgac   900
ccagacgtcc agatcagctg gtttgtgaac aacgtggaaa tacacacagc tcagacacaa   960
acccatagag aggattacaa cagtactatc cgggtggtca gcaccctccc catccagcac   1020
caggactgga tgagtggcaa ggagttcaaa tgcaaggtca acaacaaaga cctcccatca   1080
cccatcgaga gaaccatctc aaaaattaaa gggctagtca gagctccaca agtatacatc   1140
ttgccgccac cagcagagca gttgtccagg aaagatgtca gtctcacttg cctggtcgtg   1200
ggcttcaacc ctggagacat cagtgtggag tggaccagca atgggcatac agaggagaac   1260
tacaaggaca ccgcaccagt cctggactct gacggttctt acttcatata tagcaagctc   1320
aatatgaaaa caagcaagtg ggagaaaaca gattccttct catgcaacgt gagacacgag   1380
ggtctgaaaa attactacct gaagaagacc atctcccggt ctccgggtaa atga          1434
```

```
SEQ ID NO: 2                    moltype = AA   length = 477
FEATURE                         Location/Qualifiers
source                          1..477
                                mol_type = protein
                                organism = synthetic construct
SEQUENCE: 2
MECNWILPFI LSVTSGVYSQ VQLQQSGAEL ARPGASVKLS CKASGYTFTS YWMQWVKQRP   60
GQGLEWIGAI YPGDGDTRYT QKFKGKATLT ADKSSSTAYI QLSSLASEDS AVYYCARFPA   120
DGSYSYAMDY WGQGTSVTVS SAKTTPPSVY PLAPGCGDTT GSSVTLGCLV KGYFPESVTV   180
TWNSGSLSSS VHTFPALLQS GLYTMSSSVT VPSSTWPSQT VTCSVAHPAS STTVDKKLEP   240
SGPISTINPC PPCKECHKCP APNLEGGPSV FIFPPNIKDV LMISLTPKVT CVVVDVSEDD   300
PDVQISWFVN NVEVHTAQTQ THREDYNSTI RVVSTLPIQH QDWMSGKEFK CKVNNKDLPS   360
PIERTISKIK GLVRAPQVYI LPPPAEQLSR KDVSLTCLVV GFNPGDISVE WTSNGHTEEN   420
YKDTAPVLDS DGSYFIYSKL NMKTSKWEKT DSFSCNVRHE GLKNYYLKKT ISRSPGK       477
```

```
SEQ ID NO: 3                    moltype = DNA   length = 717
FEATURE                         Location/Qualifiers
source                          1..717
                                mol_type = other DNA
                                organism = synthetic construct
SEQUENCE: 3
atggagtcag acacactcct gctatgggtg ctgctgctct gggttccagg ctccactggt   60
gacattgtgc tgacccaatc tccagcttct ttggctgtgt ctctaggaca gagagccact   120
atcttctgca gagccagcca gagtgtcgat tataatggaa ttagttatat gcactggttc   180
caacagaaac caggacagcc acccaaactc ctcatctatg ctgcatccaa cctagaatct   240
gggatccctg ccaggttcag tggcagtggg tctgggacag acttcaccct caacatccat   300
cctgtggagg aggaagatgc tgcaacctat tactgtcagc aaactattga ggatccattc   360
acgttcggct cggggacaaa gttggaaata aaacgggctg atgctgcacc aactgtatcc   420
atcttcccac catccagtga gcagttaaca tctggaggtg cctcagtcgt gtgcttcttg   480
aacaacttct accccaaaga catcaatgtc aagtggaaga ttgatggcag tgaacgacaa   540
aatggcgtcc tgaacagttg gactgatcag gacagcaaag acagcaccta cagcatgagc   600
agcaccctca cgttgaccaa ggacgagtat gaacgacata acagctatac ctgtgaggcc   660
actcacaaga catcaacttc acccattgtc aagagcttca acaggaatga gtgttag       717
```

```
SEQ ID NO: 4                    moltype = AA   length = 238
FEATURE                         Location/Qualifiers
source                          1..238
                                mol_type = protein
                                organism = synthetic construct
SEQUENCE: 4
MESDTLLLWV LLLWVPGSTG DIVLTQSPAS LAVSLGQRAT IFCRASQSVD YNGISYMHWF   60
QQKPGQPPKL LIYAASNLES GIPARFSGSG SGTDFTLNIH PVEEEDAATY YCQQTIEDPF   120
TFGSGTKLEI KRADAAPTVS IFPPSSEQLT SGGASVVCFL NNFYPKDINV KWKIDGSERQ   180
NGVLNSWTDQ DSKDSTYSMS STLTLTKDEY ERHNSYTCEA THKTSTSPIV KSFNRNEC      238
```

METHOD AND KIT FOR DETECTING THE PRESENCE OF SILVER LEAF DISEASE *CHONDROSTEREUM PURPUREUM* FUNGUS

CROSS-REFERENCE TO RELATED APPLICATIONS

This application claims priority of U.S. Provisional Application No. 63/394,495 filed on Aug. 2, 2022 under 35 U.S.C. § 119(e), the entire contents of all of which are hereby incorporated by reference.

REFERENCE TO AN ELECTRONIC SEQUENCE LISTING

The content of the electronic sequence listing (2024-01-02-Sequence-Listing.xml; Size: 7,370 bytes; and Date of Creation: Jan. 2, 2024) is herein incorporated by reference in its entirety.

BACKGROUND OF THE INVENTION

Field of the Invention

The present invention relates to an antibody that is used to detect the presence of the *Chondrostereum purpureum* fungus in a plant sample, where said antibody specifically binds to the endolipogalacturonase enzyme produced by *Chondrostereum purpureum* (anti-endoPG from now). It falls within the scope of the invention, a kit and a method to detect fungal antigens, particularly, to detect the presence of the silverleaf disease (caused by the *Chondrostereum purpureum* fungus) in fruit trees, by means of detection of the endoPG enzyme through the binding of said antigen to the antibody that is described on the invention, functionalized with gold nanoparticles, where said binding is detected via enzyme-linked immunosorbent assays (ELISA) or an immunochromatographic lateral flow assay.

BRIEF DISCUSSION OF THE RELATED ART

The "silverleaf" disease on fruit crops is a widely known disease that mainly affects fruit crops such as peach, nectarine, cherry, pear, kiwi, raspberry and blueberry trees, some ligneous trees, among others (Grinbergs et al. 2019, 2020, 2021).

In Chile, it has been reported that the silver leaf disease is present in more than the 90% of tree orchards in apple crops, that has led to a decrease in crop yields, particularly, decrease in the apple crop yield, represent a CLP$200.939/ha cost, and CLP$602.813 in returns to the producer. In the case of blueberries, the crop yield reduction ranges around 40%, and losses due to this disease may account for CLP$4.501.005/ha in returns to the producer (INIA, 2016) (France et al., 2016). It is necessary to point out that the main problem that this disease poses is that it goes unnoticed in orchards, due to lack of symptoms during the early stages of plant growth, for this reason, when the disease is detected, losses in crop yield can reach up to 80%, which has an approximate cost of CLP$20.505.818/ha in apples and CLP$9.227.614-CLP$12.987.013/ha in blueberries (INIA, 2018).

Trees affected by silverleaf disease show symptoms such as weaker branches and foliage discoloration, inducing silver-greyish colour symptoms on leaves. Initially, the fungus reaches wounds of woody tissues, colonizing ligneous tissue and causing discoloration and necrosis in the xylem tissue. Foliar symptoms, such as leaves looking grayish or silver colored, are visible after two or three seasons after infection and are caused by the endopolygalacturonase produced by the pathogen, leading to the disorganizing of leaf tissues and causing detachment of the epidermis from the mesophyll, forming an airspace layer that, when refracting sunlight, leads to the silver-greyish color on leaves (France et al., 2016., Grinbergs et al., 2019, 2021a, 2021b.

Initially, when the infection occurs on lateral branches, the above-mentioned symptoms spread to a few branches and then reach the entire plant. When plants get infected in nurseries, it is highly likely for foliage symptoms to appear in an early and generalized manner, but it is difficult to distinguish from other types of pathogens or other types of plant stress conditions.

The silverleaf disease is caused by the *Chondrostereum purpureum* fungus, a widely distributed pathogen in Mediterranean climates. The morphological damages that are caused by this fungus are mainly due to the effects of an endopoligalacturonase (endoPG) toxin secretion, which migrates through the xylem to the leaves; producing the detachment of the foliar lamina from the palisade parenchyma, producing an airspace, giving the foliage a silver appearance due to the optical effect of light passing through this chamber. (Rojo et al., 2017). On the other hand, the pathogen can survive on infected trees and, after their death, can develop in dying trunks, forming their characteristic basidiocarps (spore-producing structures) (Portal Frutícola, 2019).

In general, disease control strategy is preventive and consists in injury inflicting prevention in young nursery and garden plants, such as, for example, protection of injuries due to engraftments and/or decapitation with pruning protective fungicide paste formulations, to avoid fungus entrance to the plant (Portal Frutícola, 2019). Another pathogen management strategy is by biocontrol using organisms such as *Trichoderma* or *Gliocadium*, through the addition of pellets with these fungi to infected tree trunks or branches, or through injection of a liquid formulation of said controlling agents, this last strategy has showed promising results (Portal Frutícola, 2019). Moreover, as it was previously stated, this disease is asymptomatic on the early years of the plant, so it is not possible to detect at first sight. For this reason, it is of great importance to develop fungus detection systems in order to decrease loss of crop yields and their associated economic losses.

So far, there are assays that exist to determine the presence of analyte molecules via immunochromatographic lateral flow or antigen-binding antibody based assays.

The U.S. Pat. No. 5,187,064 document discloses a method to produce antibodies using a hybridoma for detection of *Sclerotinia* in plants. The detection method comprises forming a complex between an antigen and the antibody; forming a tertiary complex and then detecting the presence of said tertiary with an analytically detectable reagent.

The WO2018097796A1 document discloses a device to determine or quantify the presence of an analyte molecule, virus cell of interest in a sample. The document also discloses a method to determine or quantify the presence of an analyte molecule, virus or cell of interest in a sample, a method of preparing the device of the invention, the use of the device of the invention for determining or quantifying the presence of an analyte molecule, virus or cell of interest in a sample and a kit of parts comprising the device of the invention. Fungi detection is within the scope of this method.

The WO2014174085 document describes a device for measuring the concentration of analytes in liquid samples such as bodily samples, where fungi detection is possible. The device comprises an application zone, to which a sample can be applied, and which contains a specific molecule capable of specifically binding the analyte of interest, said specific molecule being conjugated to a reporter which can give rise to variations in impedance. The resulting complex migrates by capillarity and enters a detection zone, on which another molecule capable of specifically binding the analyte of interest is immobilized. The concentration of reporter molecules in the detection zone is proportional with the concentration of analyte in the sample, and variations in concentration of reporter molecules yield a measurable change in electrical properties such as a change in impedance and/or capacitance which can be correlated to the concentration of analyte. The device is useful for monitoring concentrations of analytes that are biological markers for bacterial, viral or fungal infections, diseases or medical conditions, or their severity, in animals such as humans, farm animals, fish and pets, and in plants.

Another example is the WO2016035099 document that discloses a flow through device for detection and differentiation of multiple bioanalytes from a single sample and a process thereof. The device is a visual, rapid, sensitive and reliable immunoassay analyzer for the differential detection of multiple bioanalytes in biological fluids like human blood, serum or plasma by immobilizing the respective disease specific bio-molecules i.e. antigen, antibody, peptides, synthetic or recombinant peptides and/or proteins derived from disease causing microorganisms on the immunofilteration reaction membrane.

The U.S. Pat. No. 5,563,040 document describes a method and apparatus for detecting incipient fungal decay in wood via detection with an anti-xylanase monoclonal antibody and a substrate antigen in wood extracts. The device has the anti-xylanase monoclonal antibody immobilized in a defined capture zone to a polyester assay substrate. Wood extract to be tested is applied to the end of the polyester substrate and allowed to flow laterally through the carrier zone and the capture zone. A positive test results when antigen in the wood extract is complexed by the labeled polyclonal and monoclonal antibodies to form an observable particle complex.

In the particular case of immunochromatographic lateral flow assays, the U.S. Pat. No. 93,613,307 document discloses an assay and product for rapid detection of fungi in a variety of samples suspected of containing fungi. Even if the invention is focused on swab samples from the human vaginal area, it is described that it can be used also in other environments such as in food and feeds. The invention includes an assay for detection of the presence of a fungus in a sample, by utilizing an antibody that reacts with a deep-seated glucan fungal antigen in an immunochromatographic lateral flow assay system.

The CN201911121513 document discloses a time-resolved fluorescence kit for synchronously detecting three fungaltoxins diacetoxyscirpenol, aflatoxin b1 and sterigmatocystin. This time-resolved fluorescence kit comprises an immunochromatography time-resolved fluorescence test strip and a sample reaction bottle containing an europium-labeled monoclonal antibody resistant to diacetoxyscirpenol, aflatoxin B1 and sterigmatocystin. The strip includes a water absorption pad, a detection pad and a sample pad. The detection pad uses a nitrocellulose membrane as a base pad, a quality control line and detection lines are transversely provided on the nitrocellulose film.

One of the new described alternatives or technological developments for antigen immunodetection is via the use of conjugated immunodetection complexes or nanoparticle-functionalized complexes.

The WO2017037408 document discloses an assay for determining the presence and/or concentration of an antigen in a sample. For this, nanoparticles functionalized with one of an antigen and an antibody specific for the antigen, and a luminescent metal complex which may be a FRET (Förster resonance energy transfer) donor, are provided. It is within the scope of the WO2017037408 document an assay for determining the presence and/or concentration of the antigen in a sample comprises mixing the functionalized nanoparticles with a FRET acceptor conjugated to the other of the antigen and the antibody specific for the antigen, measuring a first fluorescence signal of the mixture, adding a quantity of the sample to the mixture, and measuring a second fluorescence signal of the mixture. Any difference between the first and second fluorescence signals is indicative of the presence of the antigen in the sample. The document makes no reference to the detection of fungal or *Chondrostereum purpureum* antigens.

The US2016299136 document discloses a method for performing single step assays for the determination of the presence or absence of an analyte in a liquid sample, on a solid surface. This method comprises an aptamer coated and signal molecule loaded porous silica particles immobilized on a porous solid material. Specific interaction of the analyte with the aptamers coated on the silica beads, cause release of the signal molecules which result in a detectable signal on the solid support. Also provided are assay devices for the detection platform. It is within the scope of this document the detection of spores and fungal cells.

Accounting for the detection of fungal antigens using nanoparticle-based immunochromatographic complexes, for example the US 2016273055 document discloses an efficient and quick method for the identification of a fungus in a sample such as a plant tissue, where said invention is based on nanoparticles (gold nanoparticles or silver nanoparticles) that detect a target nanoparticle specific for a fungus such as *Raffaelea lauricola*. The assay comprises the steps of obtaining nucleic acids from the sample, contacting the nucleic acids obtained from the sample with a single stranded nucleic acid (ssNA) probe complementary to a target nucleic acid specific for the fungus, and adding nanoparticles to the mixture. The presence of the target nucleic acid in the nucleic acids obtained from the sample, and hence the presence of the fungus in the sample, is indicated by a particular color associated with aggregated nanoparticles in the solution. The document also discloses a detection kit based on the described complex.

As for the specific detection of *Chondrostereum purpureum*, the US20200299752 document discloses a method to determine quantification conditions for a microorganism in a sample, where said method includes the detection of several microorganisms, *Chondrostereum* genus fungi, within its scope. Even though this document is generic and includes the possibility of detection using an ELISA assay, the main scope of this document is based on PCR-detection. The method described in this document is not focused on fast field detection.

So far, the described methods and kits in the state of the art for immunochromatographic detection include a generic detection of analytes or antigens, not being specifically defined for the detection of a fungal antigen in particular. Moreover, even if immunochromatographic detection complexes based on nanoparticle conjugation or functionalization of antibodies to reveal the antigen-antibody reaction have been described, methods or kits particularly directed to the *Chondrostereum purpureum* detection have not been described.

Also, there are no records on the state of the art or teachings that would allow to define the conditions to propose a field test method and kit for the detection of *Chondrostereum purpureum*, in directly extracted wood and leaves samples of species of commercial interest. There are no available field test kits or quick application tests.

SUMMARY OF THE INVENTION

The invention relates to an antibody used to detect the presence of the *Chondrostereum purpureum* fungus in a plant sample, where said antibody specifically binds to the *Chondrostereum purpureum* endolipogalacturonase (anti-endoPG from now on). The antibody described in the present invention is comprised by a heavy chain and a light chain. The heavy chain of said antibody has a nucleotidic sequence represented by SEQ ID. 1 and an aminoacid sequence represented by SEQ ID. 2. On its part, the light chain of said antibody has a nucleotidic sequence represented by SEQ ID. 3 and an aminoacid sequence represented by SEQ ID. 4.

The antibody within the scope of the invention, can be synthetized through any process that allow for synthetic antibody production. It is known that it is possible to synthesize an antibody when its nucleotidic and aminoacidic sequences are defined.

Its chemical synthesis is possible through molecular methods for transformation of microorganisms or host organisms that produce the antibody, methods that rely on recombinant bacterial, animal, or human cells or hybridomas for production of antibodies. A variety of different host organisms are considered, including *E. coli, Saccharomyces cerevisiae, Pichia pastoris*, cells from insects, algae, plants, and cells from mammals. Cell-free systems are included as methods for generating genomic libraries, and with a cell-free production denomination.

The antibody within the scope of the invention can be conjugated or bound to nanoparticles, particularly, gold nanoparticles. It falls within the scope of the invention an antibody that is bound or conjugated with gold nanoparticles through one L-cysteine residue to conform a complex comprised by gold nanoparticles bound through L-cysteine to the antibody (NpsAu+Lc+Ab complex).

As per reach of the scope of the invention, gold nanoparticles that are conjugated to the antibody have an average diameter of 25 nm and a surface charge of −19.9 mV.

The present invention also relates to a method to detect the presence of the *Chondrostereum purpureum* phytopathogen fungus in a plant sample and to an immunochromatographic kit for rapid detection of the *Chondrostereum purpureum* fungus.

The method comprised in the present invention allows for the detection of the endopolygalacturonase (endoPG) enzyme produced by the *Chondrostereum purpureum* fungus that is responsible for the foliar symptoms of the silver leaf disease on fruit trees. To detect the fungus, nanoparticle conjugated or functionalized antibodies, in particular gold nanoparticles bound by a L-cysteine residue (anti EndoPG antibody/L-cysteine/gold nanoparticle complex, NpsAu+Lc+Ab or NpsAu+Lc+Ab complex hereafter) are provided.

Particularly, the method for detection of the *Chondrostereum purpureum* fungus on plant samples comprises the following steps or stages:

a. Preparing the vegetable or tree tissue sample of interest to obtain a supernatant from the sample,
b. Establish contact between the sample supernatant to be analyzed with an antibody that specifically binds to the *Chondrostereum purpureum* endopolygalacturonase (anti-endoPG) enzyme, where said antibody is in turn conjugated with gold nanoparticles bound by a L-cysteine residue (NpsAu+Lc+Ab complex), and
c. evaluate the specific union of the anti-endoPG antibody, where the sample contains the fungus if the antibody is specifically bound to the sample.

To evaluate the specificity of the anti-endo PG, a method selected the group that consists on lateral flow immunochromatography or ELISA procedures is selected to be used.

A kit for rapid field detection of the *Chondrostereum purpureum* phytopathogen fungus also falls within the scope of this document. The kit corresponds to an immunochromatographic kit, in particular, corresponds to lateral flow immunochromatographic assays.

The kit for the fast detection of the *Chondrostereum purpureum* fungus in a plant sample is comprised by a reactive strip composed of a nitrocellulose membrane where there are differentiated areas for the sample pad, test zone, control zone and absorption pad placements. The test zone and the control zone contain the *Chondrostereum purpureum* anti-EndoPG primary antibodies conjugated with gold nanoparticles and the detection secondary antibodies. As detection secondary antibodies anti-rabbit IgG antibodies are provided.

The kit also comprises its instructions of use.

Functioning of the kit comprises diffusion through a nitrocellulose membrane of nanoparticles to an enzymatic extract, where the NpsAu+Lc+Ab complex is rehydrated and is mixed with the sample to be analyzed. When the sample contains endoPG it is recognized by the antibody and this complex diffuses until it is captured by an anti-endoPG antibody, which is immobilized in the membrane.

When an anti-endoPG complex excess exists, said complex keeps on diffusing and reacts with the anti-rabbit IgG secondary antibody, developing a red color considered as a control test and validating the method of detection.

When the presence of endoPG does not exist in the sample, red color will appear only on the control zone, due to the anti-endoPG complex not moving.

In particular, the detection test will be considered as a positive when after dispensing the sample on the sample deposit pad of the nitrocellulose membrane and after waiting for the reaction to complete two red lines appear, one in the test zone and another one in the control zone.

Kit detection is based on the diffusion of conjugated gold nanoparticles through the nitrocellulose membrane, that by means of capillary diffusion move towards specific adsorption sites for enzyme detection by primary and secondary antibodies that are immobilized onto it. The reaction used a synthetic endoPG1, which reacted with the lines that contained NpsAu+Lc+Ab complex on the nitrocellulose strip and with the control line.

The detection kit allows for rapid detection of *Chondrostereum purpureum* in field plant samples, in a qualitative manner.

To demonstrate the proper functioning of the proposed detection kit, the inventors validated the prototype in the laboratory using blueberry samples from Vilcún, and apple tree samples from Chillán, naturally infected with *C. purpureum*, and also artificially inoculated plants with virulent strains of the fungus. For the negative control, in vitro plant leaves were used. A 1 g leaf sample was prepared, which was processed to obtain its supernatant. Then, an extract of the supernatant was added to the nitrocellulose membrane containing the antibodies.

The results of the validation allow to establish that, in both of the evaluated fruit species, an approximate reaction time of 20 min for detection was observed (example 5).

The method and kit allow for rapid and in-field detection of *C. purpureum* fungus presence in plant tissue, particularly fruit plants. The use of the kit is proposed because it allows for the *C. purpureum* fungus in-field detection with a detection time of 20-30 min. These characteristics allow to establish that the antibody, method, and kit allow for detection of the *C. purpureum* fungus in a short time and directly on the field, in such a way, that contaminated crops can be detected almost immediately, allowing for quick, effective and in situ decision-making. The antibody, method and kit described as part of the invention address the technical issue of having tools available for quick and in-field detection of the *C. purpureum*. fungus. In the closest state of the art, any similar or equivalent solutions cannot be found.

A complex comprised by the anti EndoPG antibody conjugated with gold nanoparticles bound by a L-cysteine residue (anti EndoPG antibody/L-cysteine/gold nanoparticle complex) falls within the scope of the invention. This complex has been developed by the inventors to be part of the already described *Chondrostereum purpureum* fungus presence detection method and rapid detection kit.

The anti EndoPG antibody corresponds to a monoclonal antibody defined by its aminoacidic and/or nucleotidic sequences.

In the anti EndoPG antibody/L-cysteine/gold nanoparticle complex, gold nanoparticles have an average diameter of 25 nm and a surface charge of −19.9 mV.

The samples to be analyzed by the described kit and method correspond to leaf or wood samples, preferably fresh leaves. The fresh leaf sample to be analyzed, must be crushed and processed to obtain a supernatant, that is dispensed on the sample pad of the detection system. Sample preparation consists on crushing fresh leaves or wood (1 g), macerating in buffer (1×PBS) and washing with an organic solvent such as acetone.

The residue is resuspended in 1×PBS buffer and stirred. Finally, the pellet is discarded and the supernatant, that constitutes the enzymatic extract that reacts with the components on the reactive strip of the kit, is retained.

In the present invention, the detection method and kit includes endoPG identification on fruit tree samples such as apple, kiwi, blueberry, pear and raspberry. In other embodiments of the invention, the detection kit may include endoPG identification in fruit trees from the *Malus* sp, *Vaccinium* sp, *Pyrus* sp, *Actinidia* sp, *Rubus* sp, *Prunus* sp genus.

Definitions

When the present document makes reference to the "plant tissue", "plant sample" or "plant tissue sample" terms, it is referring to all those samples that come from a plant organism to be analyzed. In particular, a plant sample can be obtained from mature plants, young plants, trees, tree trunks, wood residues, seeds, flowers, tubers or any other plant materials that could be used as sample.

When the present document makes reference to the "presence" or "pathogen presence" or "fungus presence" terms, it is indicating that the fungus has infected, penetrated and colonized the plant. Fungus presence is visible when plant tissue results damaged. In the case of "pathogenic fungus" it is making reference to fungi that infect plants and that cause diseases on them.

When the present document makes reference to the "nanoparticle" term, it is referring to any particulate material smaller than 100 μm and that can have different uses. On this case, nanoparticles correspond to gold nanoparticles.

When the present document makes reference to the "antibody" term, it refers to those protein components of the immune system that circulate in the blood and tissue fluids of vertebrates. They have the capacity to recognize and bind to foreign or exogenous substances. In the case of the present invention, an "antibody" is used for the detection of a substance secreted by the pathogenic fungus, this allowing for pathogen presence identification in a plant sample and determining if the sample derives from an infected plant.

When the present document makes reference to the "conjugation" or "conjugated antibody" it is indicating that said antibody is chemically linked to a particular substance that can be a chemical substance. In the case of the present invention, the antibody is conjugated with a compound that allows for it to bind to the nanoparticle and taken together present the properties necessary for pathogenic fungus detection.

When the present document makes reference to the "anti endoPG antibody" term, it is referring to that antibody that is capable of recognizing the endoPG endoplygalactu- ronases) lytic enzyme present in the fungus, where presence of the enzyme is indicative of the disease caused by the pathogenic fungus in plants.

The term "reducing agent" is understood as any chemical compound that allows for electron transfer, particularly, a reducing agent releases electrons that are accepted by an oxidizing agent generating a reduction-oxidation reaction, where the reducing agent loses electrons and is oxidized.

When the present document makes reference to the "detection" term, it is making reference to the action of searching, tracking or exploring a molecule, compound, etc. in a determined sample. When the document makes reference to the "rapid detection" term it is indicating a searching, tracking and/or exploring method of a particular molecule or substance that delivers results in a short time. This document also references the "field detection" term, referring to the action of searching, tracking and/or exploring of an agent, molecule or substance in particular that can be collected on real time and within its habitat.

When the present document makes reference to the "reaction time" term, it is indicating the response time or time elapsed since the commencement of a chemical reaction until the final product is obtained, provided the chemical reaction was fully completed.

When the present document makes reference to the "ELISA" term, it is referencing to the immunoassay for detecting a substance, molecule or antigen that is based on its union with an antibody that recognizes it specifically, that in turn is linked to an enzyme which emits a detectable chemiluminescent, color or another chemical reaction product. The use of a detection secondary antibody for the primary antibody, where the secondary antibody is linked to the enzyme that produces a detectable product for establishing the antigen-antibody union falls within the scope of this invention.

When the present document makes reference to the "immunochromatography" term, it is referring to an antibody-based diagnostic method, which is quick and simple. Immunochromatography is based on contacting a sample to a conjugate zone in a nitrocellulose membrane, which is comprised by an antibody specifically binding to antigen of interest and a reagent for its detection. Moreover, when the present document makes reference to the "lateral flow chromatography" it refers to the technical foundations of immunochromatography (based on the antigen-antibody union) where the reaction strip is submerged on a liquid sample for detection on it.

When the present invention makes reference to the "kit" term it is referring to any set of pieces, elements, objects, materials and/or devices that complement their use and function, and that given instructions of use in a leaflet can be used by whoever wishes to.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention.

a) The graph shows the UV/Vis spectra of 200 μM pure L-cysteine.

b) in the L-cysteine functionalized nanoparticles UV/Vis spectra graph it is possible to observe an increase in functionalized samples (pink, light blue, green, red) in respect to NPs-Au (shown in yellow).

Figure 5A:
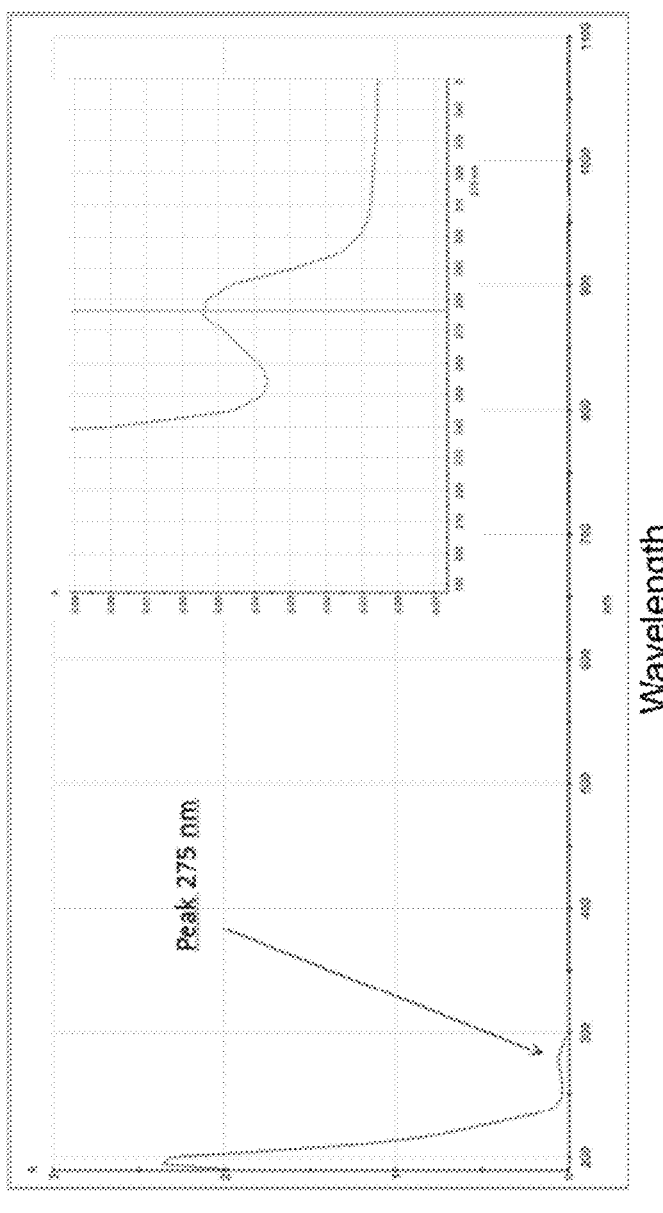
Figure 5B:
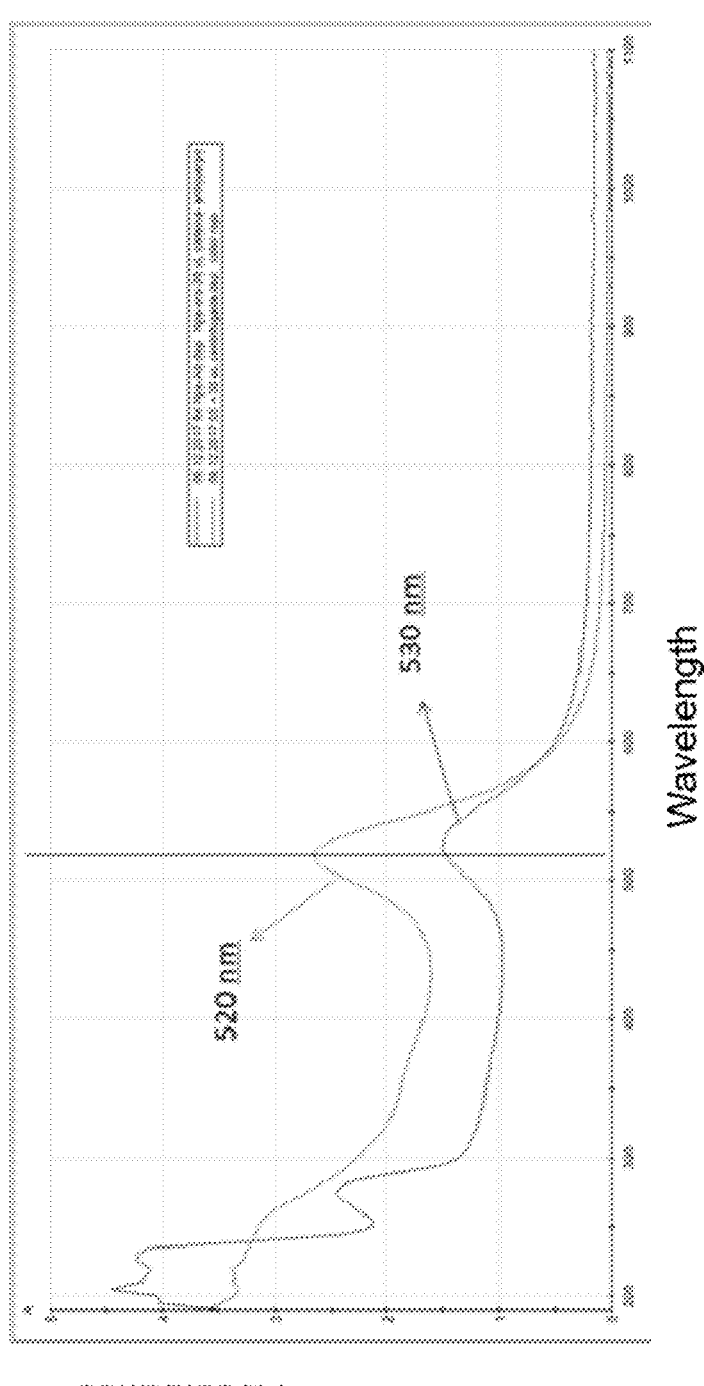

FIGS. 5A-5B: UV-VIS spectra of functionalized NPsAu conjugated with the antibody. a) the figure shows the UV/Vis spectra of the antibodies. b) the figure shows the UV-VIS spectra of the functionalized nanoparticles that were conjugated to the antibody. In blue, functionalized nanoparticles without antibodies can be observed, while the NPsAu-L-cysteine-antibody complex can be observed in red.

Figure 6A:
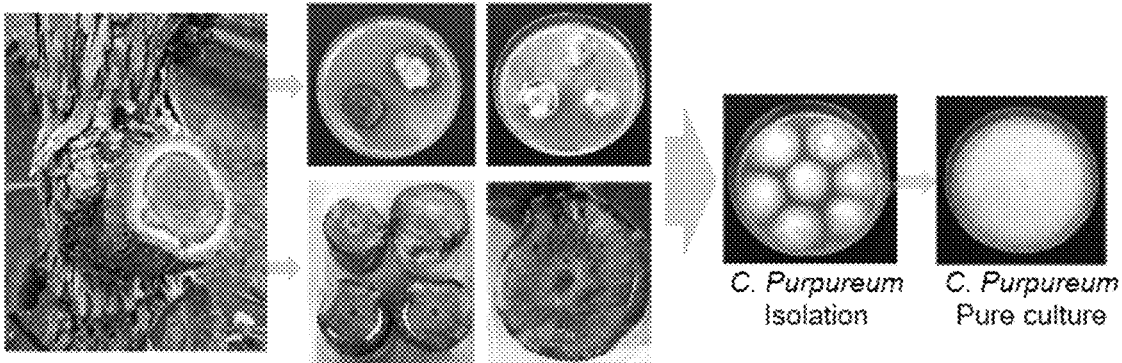
Figure 6B:
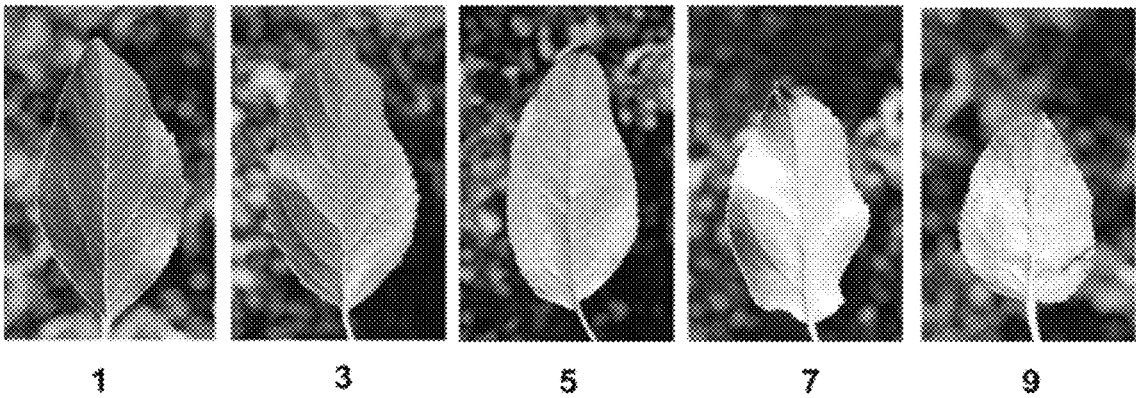

FIGS. 6A-6B: *Chondrostereum purpureum* isolation from wood and leaf samples. A) wood sample collection and their conditions are presented, which were used for isolation of the *C. purpureum* by seeding in aAPD agar solid media. B)

collected leaf samples are shown for follow up of disease onset signs and to generate a scale for symptom severity, where 1 corresponds to healthy and 9 to maximum amount of symptoms.

Figure 7:
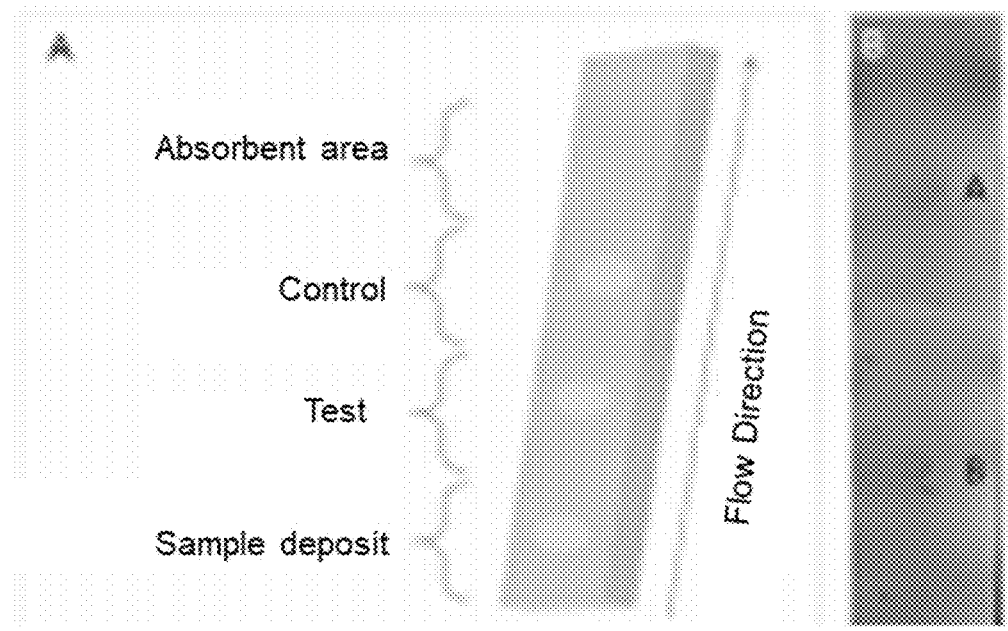
Figure 7:
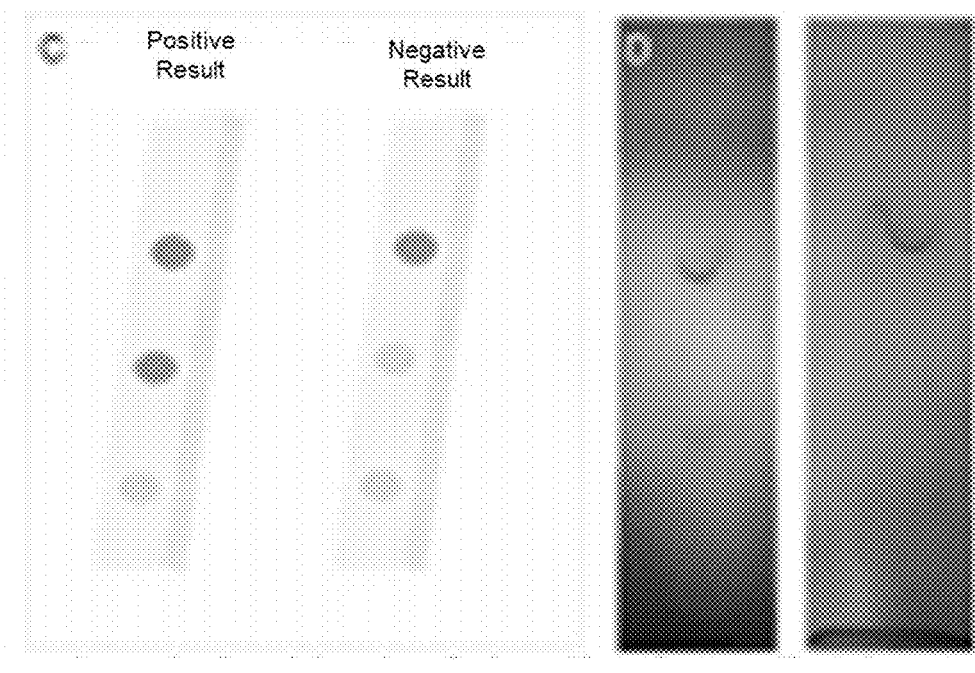

FIG. 7: Silver leaf detection kit. A) components of the flow device, b) enzyme detection via primary antibody, c) diagram for the interpretation of the kit results, d) validation test on the nitrocellulose membrane, to the left a positive orchard sample and to the right a negative control.

DETAILED DESCRIPTION OF THE PREFERRED EMBODIMENTS

APPLICATION EXAMPLES

Example 1: Functionalized Gold Nanoparticle Synthesis and Production of the Functionalized Nanoparticle-Immobilized Antibody The first step for developing the detection kit comprises gold nanoparticles synthesis.

Part of the detection kit comprises gold nanoparticles and a reducing agent, producing a stable colloidal solution. For that purpose, monodisperse colloidal gold was synthetized using the modified Turkevich method. 6 different tetrachloroauric acid and trisodium citrate aqueous solutions were prepared, and different $HAuCl_4$ and trisodium citrate concentrations were evaluated to select the solution that met the desired characteristics for a gold nanoparticle (NPsAu) solution (Table 1).

TABLE 1

| | Solutions used in gold nanoparticles synthesis. | | | |
|---|---|---|---|---|
| Synthesis | Nanopure water (mL) | 25 mM $HAuCl_4$ (mL) | 1% Sodium citrate (mL) | Observations |
| S1: | 100 | 1 | 2.5 | Temperature of 95° C., citrate is added, 20 min agitation. Orange color. |
| S2 | 20 | 1 | 2 | Temperature of 95° C., citrate is added, 20 min agitation. Orange color. |
| S3 | 100 | 0.1 | 2 | Temperature of 95° C., citrate is added, 20 min agitation. Brilliant red color. |
| S4 | 100 | 0.3 | 2 | Temperature of 95° C., citrate is added, 20 min agitation. Red color, black residues. |
| S5: | 100 | 0.2 | 2 | Temperature of 95° C., citrate is added, 20 min agitation. Red color. |
| S6: | 100 | 0.2 | 4 | Temperature of 95° C., citrate is added, 20 min agitation. Red color, citrate excess. |

Figure 1A:
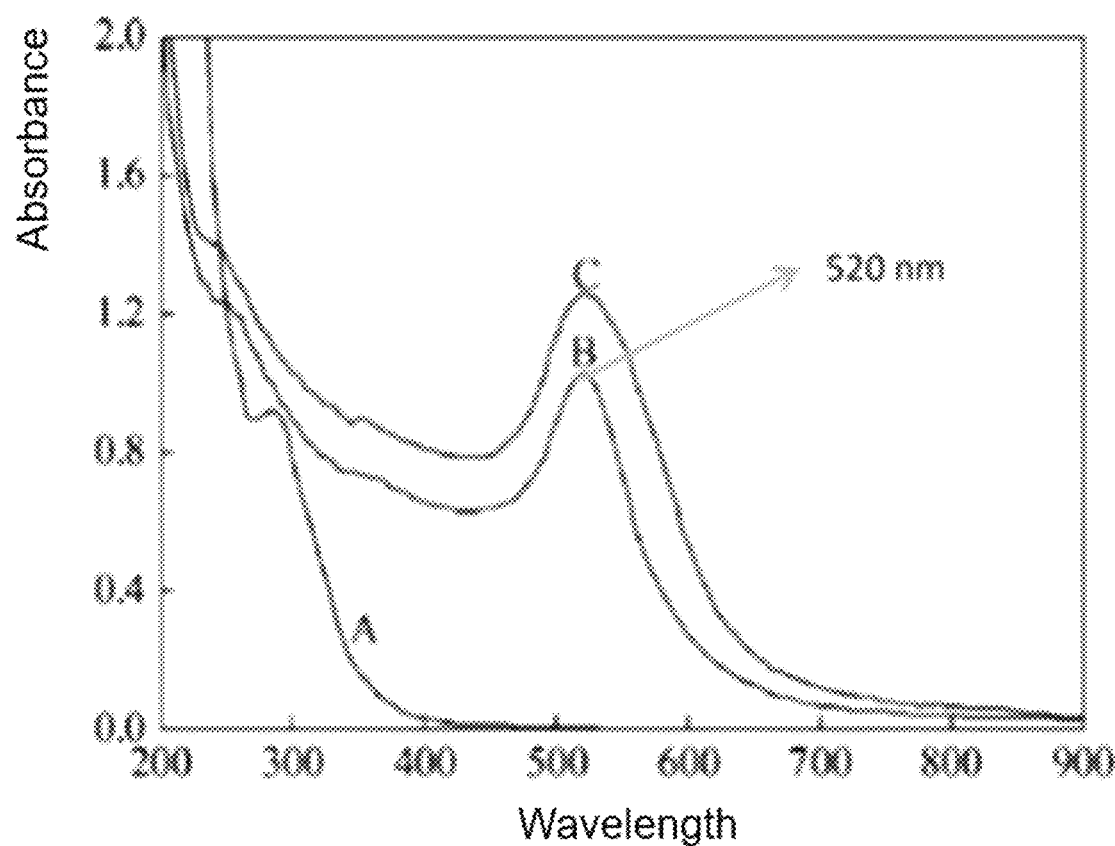
FIGS. 1A-1B: UV/VIS spectra of the gold nanoparticles obtained from the S5 synthesis. A) graph shows the optimal nanoparticle wavelength (nm) for its synthesis according to what is described in literature (P. Preechakasedkit et al.,/ Biosensors and Bioelectronics (2012) 562-566); b) graph shows wavelength characteristics of the nanoparticles obtained from the S5 synthesis; where ˷ ˷ ˷ A corresponds to the start of the spectrum and ──── B to the end of it. In B), the arrow indicates peak absorbance at 520 nm, equivalent to what is previously described in literature.
Figure 1B:
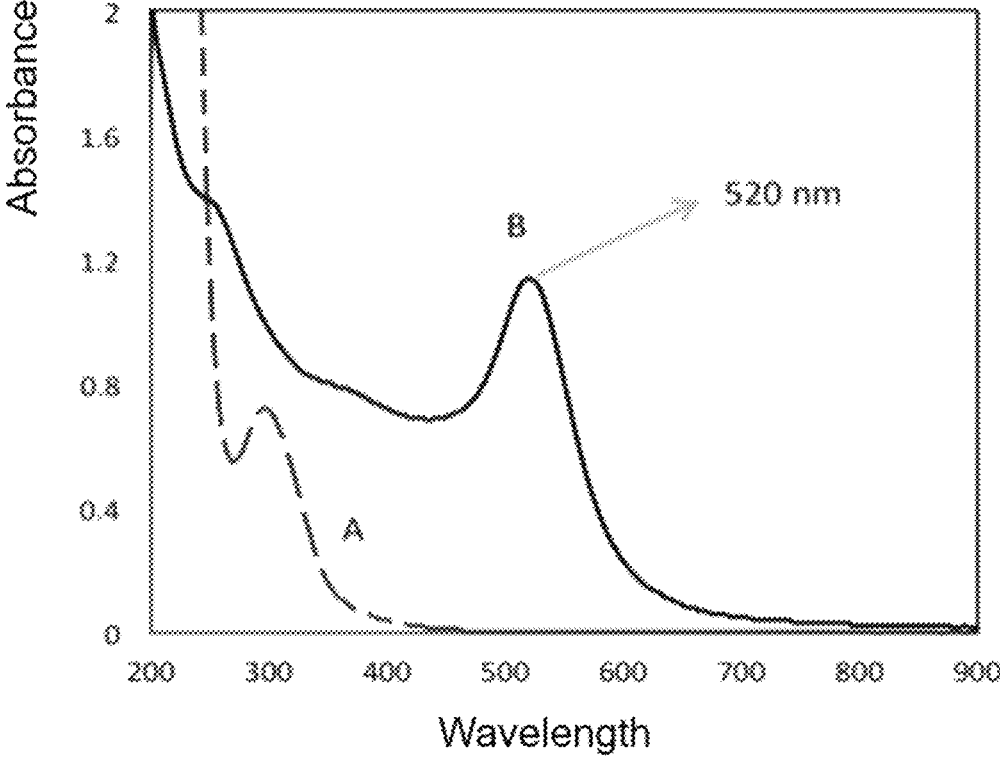

Solution characteristics were determined, according to their colorimetric properties, bright red color and a visible light spectrum absorbance (UV-VIS) wavelength peak at 520 nm. From all possible combinations from table 1, solution 5 (S5) was selected for NPsAu synthesis, because it showed Kiger colloidal stability, a bright red color, both characteristics for the absorbances reported in literature P. Preechakasedkit et al.,/Biosensors and Bioelectronics (2012) 562-566 (FIGS. 1A-1B). In any case, pre combinations were tested by modifying the citrate concentration, however, these combinations did not reveal the desired red color, so they were discarded.

Figure 2:
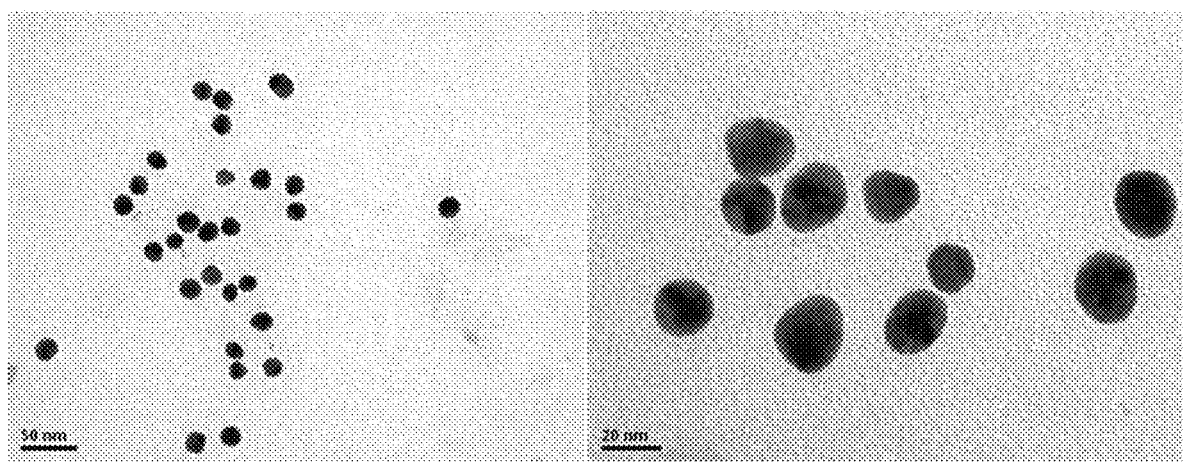
FIG. 2: TEM observation of gold nanoparticles. Nanoparticles obtained from the S5 synthesis are observed. Examination was carried out by transmission electron microscopy (TEM) determining a 25 nm average diameter.
Figure 3A:
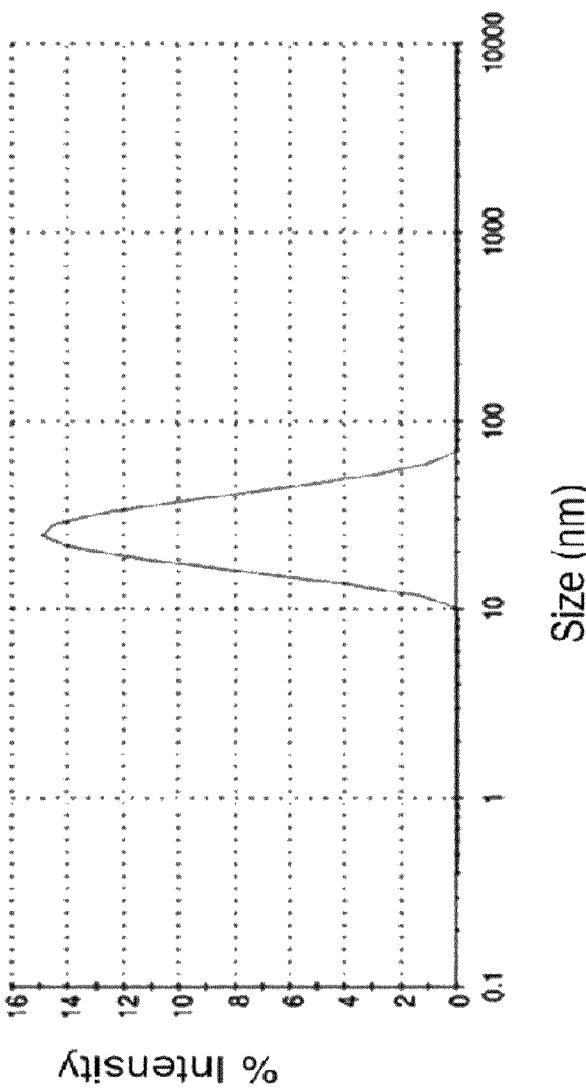
FIGS. 3A-3B: Size and dispersion distribution determination of the NPsAu. a) The graph shows diameters for the gold nanoparticles obtained from the S5 synthesis, using dynamic light scattering (DLS). b) The graph shows Z potential of the S5 nanoparticles.
Figure 3B:
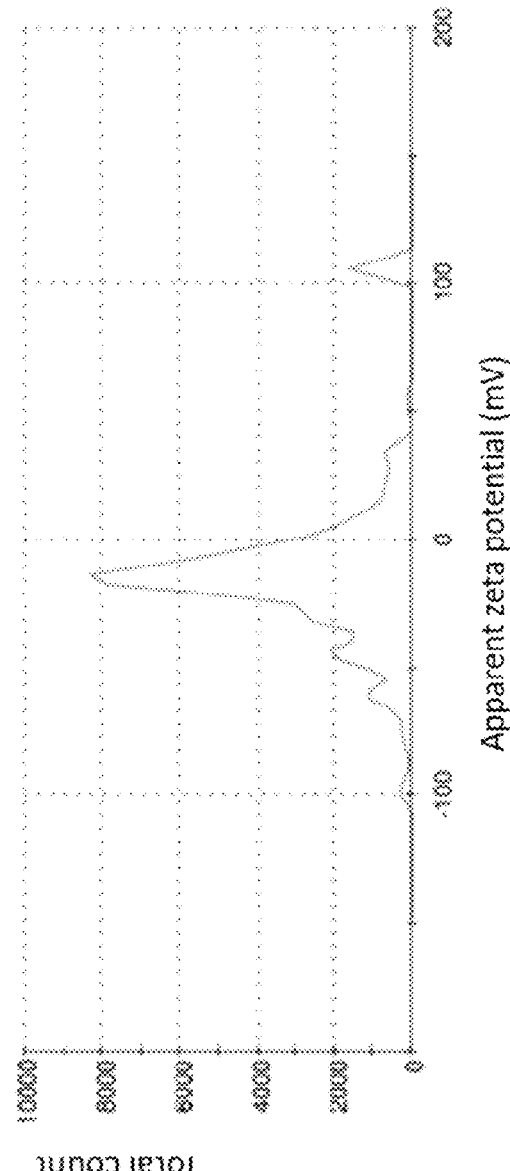

On the other hand, the NPsAu obtained through S5 synthesis were characterized with high resolution transmission electron microscopy TEM), where it was possible to observe monodispersed spherical particles with an average diameter of 25 nm (FIG. 2). Electric charge or Z potential of the nanoparticles, average size and s distribution were determined with the dynamic light scattering (DLS) method using the Malvern Zetasizer nano ZS equipment (FIG. 3A; Table 2). Results for these measurements showed that the superficial charge of the NPsAu was −19.9 mV, which is explained by the negative charges that are conferred by citrate, explaining the proper nanoparticle dispersion obtained, which presented a polydispersity index lower than 0.3 (FIG. 3B; Table 3).

TABLE 2

Size-distribution by S5 NPsAu intensity.

| Analysis conditions | | Results | |
| --- | --- | --- | --- |
| Temperature ° C. | 25.1 | Z-average (d · nm) | 23.07 |
| Count rate (kcps) | 293.7 | PdI | 0.219 |
| Measuring position | 4.65 | Intercept | 0.897 |
| | | Size | 27.22 |
| | | Intensity % | 100.00 |
| | | Standard deviation | 9.885 |

TABLE 3

Zeta potential distribution (superficial charge) of S5 NPsAu.

| Analysis conditions | | Results | |
| --- | --- | --- | --- |
| Temperature (° C.) | 25.1 | Zeta Potential (mV) | −19.9 |
| Count rate (kcps) | 97.1 | Zeta Deviation (mV) | 50.4 |
| Measuring position (mm) | 2.00 | Conductivity (mS/cm) | 0.290 |
| Zeta runs | 10 | | |

The second step corresponds to the nanoparticle functionalization, with the objective of obtaining NPsAu that can be used as diagnostic agents. Nanoparticle (NPsAu) surfaces were adapted for further conjugation with a ligand or molecule that can be used to control nanoparticle size during its synthesis and to prevent their agglomeration. In this case, the molecules used to conjugate to NPsAu correspond to antibodies, that were linked through a L-cysteine residue to the NPsAu because said residue has a carboxyl moiety that can help with the stabilization of the conjugation.

Figure 4A:
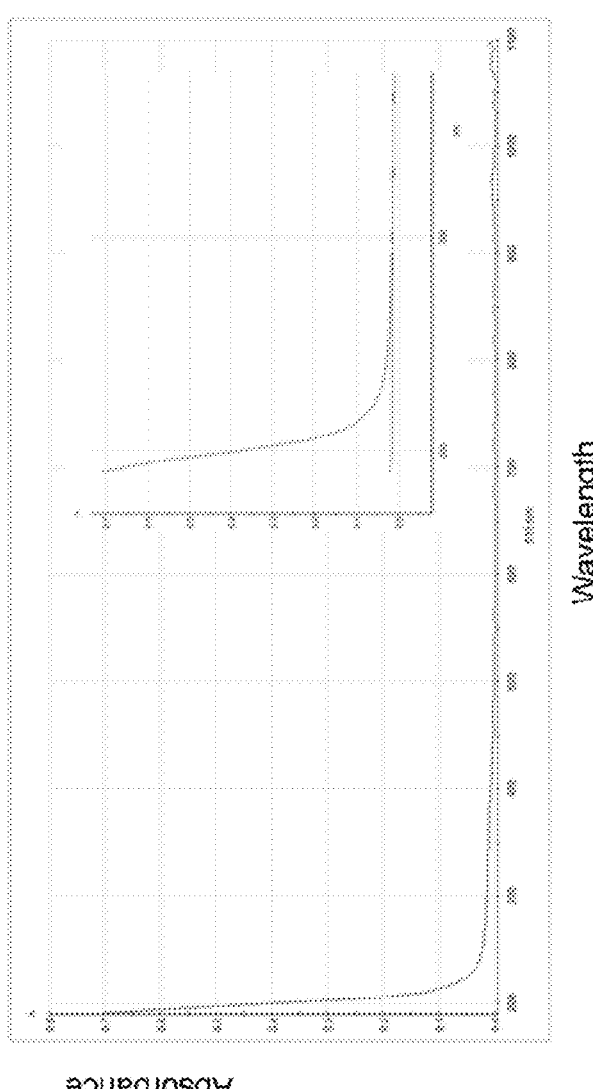
FIGS. 4A-4B: UV-VIS spectra of NPsAu functionalized with L-cysteine.
Figure 4B:
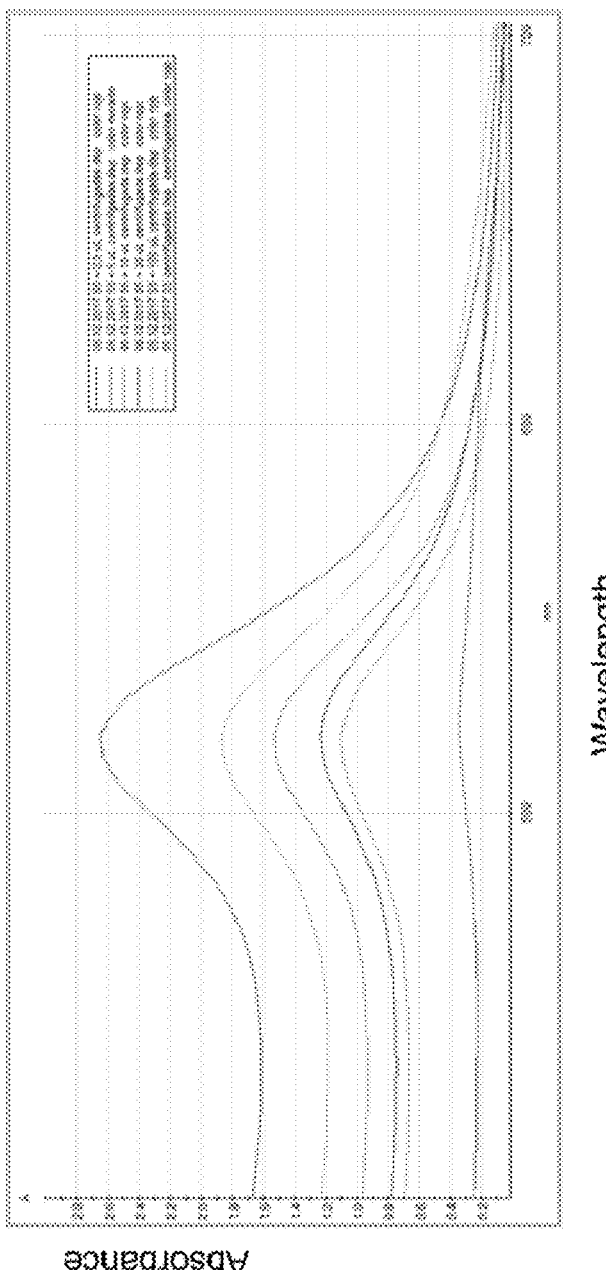

For nanoparticle functionalization, NPsAu were synthetized using the Turkevitch method, and then they were conjugated with L-cysteine starting from a 200 µM stock solution and performing dilutions (0.1; 0.2; 0.4; 1.2; 4 µM). This was performed with the objective of determining optimal liquid ligand concentration that allows to maintain particle size without them showing signs of agglomeration. Prepared solutions were stirred for 2 hours at room temperature and then were centrifuged at 10000 rpm for 15 minutes. Finally, NPsAu-cysteine UV-VIS spectra was verified using as a control the UV-VIS absorbance spectra of pure L-cysteine, where 200 µM of the latter were used (FIG. 4A). L-cysteine functionalized nanoparticles show an absorbance increase in functionalized nanoparticles (shown in pink, light blue, green, red) in respect to NPsAu (yellow) (FIG. 4B).

Endo Antibodies

The EndoPG antibody that is part of the NpsAu+Lc+Ab complex described on the present invention is comprised by a heavy chain and a light chain. The heavy chain of said antibody is comprised by a heavy chain that presents a nucleotidic sequence represented by the SEQ ID. 1 and an aminoacid sequence represented by the SEQ ID. 2

On its part, the light chain of said antibody has a nucleotidic sequence represented by SEQ ID. 3 and an aminoacid sequence represented by SEQ ID. 4.

The antibody can be synthetized through any process that allows for synthetic antibody production. It is known that it is possible to synthesize an antibody when its nucleotidic and aminoacidic sequences are defined.

Its chemical synthesis is possible through molecular methods for transformation of microorganisms or host organisms that produce the antibody, methods that rely on recombinant bacterial, animal, human cells or hybridomas for production of antibodies. A variety of different host organisms are considered, including *E. coli, Saccharomyces cerevisiae, Pichia pastoris*, cells from insects, algae, plants, and cells from mammals. Cell-free systems are included as methods for generating genomic libraries, with a cell-free production denomination.

Antibody Immobilization on Functionalized NPsAu

For antibody immobilization in functionalized NPsAu nanoparticles, an antibody solution was prepared by adding 1 mL of sterile water to lyophilized antibodies. Then, a 1:1000 dilution was performed (10 µL of antibody with 990 µL of sterile water) and was used in subsequent assays. Moreover, a wash solution consisting in 1 mL of 10×PBS with 100 µL of 10% BSA and 9 mL of sterile water was prepared.

1 mL of L-cysteine mixed with 8 µL of antibody dilution were added to 5 1.5 mL tubes and then were incubated for 30 minutes at room temperature. Then, 100 µL of 10% BSA were added to the tubes and were incubated for 10 minutes at room temperature. Subsequently, tubes were centrifuged at 20000 g for 1 hour at 4° C. The supernatant was discarded and remaining precipitate was resuspended in 1 mL of wash solution and centrifuged; the obtained pellet was resuspended in water and adjusted pH to 7.0.

Absorbance peak movement from 520 to 530 nm and a lower band intensity (less absorbance) were observed using UV/VIS absorbance (FIG. 5B). Latter results, together with the red coloring developed by the solution, indicate that the antibody immobilization on the nanoparticle was successful. It is worth mentioning that absorbance for the unconjugated antibody was also verified (FIG. 5A)

Example 2: Anti-endoPG Specificity Validated in Different Fruit Plants

To determine antibody specificity in different fruit trees, the proposed ELISA protocol was performed to detect endoPG1 produced by *C. pupureum*, in apple, blueberry, plum, cherry, peach and kiwi. To validate ELISA standardization in different fruit trees, samples were gathered from commercial orchards that were already infected with silver leaf (monthly gathering from October 2017 to May 2018) (Table 4.)

TABLE 4

Silver leaf-contaminated plant sample gathering areas for evaluation of the functionalized NPsAu specificity for endoPG.

| Host | Gathering area |
| --- | --- |
| Apple | Santa Rosa, Chillán, Biobío region. |
| Blueberry | Vilcún, Temuco, Biobío, Maule. |

TABLE 4-continued

Silver leaf-contaminated plant sample gathering areas for evaluation
of the functionalized NPsAu specificity for endoPG.

| Host | Gathering area |
|---|---|
| Kiwi | Marchant Island, Curicó, Maule. |
| Cherry | Los Guindos, Curicó, Maule. |
| Plum | Tutuquen, Curicó, Maule. |
| Peach | Pichidegua, Cahapoal, O'Higgins. |

In each of the gathering areas indicated on table 4, wood samples were collected from plants that showed foliar symptoms to isolate the pathogen. Pathogen isolation was performed by depositing samples on 25% acidified potato dextrose agar (25% aAPD, Difco), and then incubating in a moist chamber for visible signs of silver leaf disease (FIG. 6A). Besides, leaves were gathered from a 1.2 m height from ground level to be stored at –20° C. and analyzed afterwards.

In the first instance, a scale for symptom severity determination was used when examining leaves, where said scale goes from 1 to 9 and where 1 corresponds to a healthy specimen and increases as the disease does to 9 (FIG. 6B). The total number of samples that were gathered for analysis was of 430 in a 30-day period, analyzing foliar symptoms of each one of them as it is indicated in FIG. 6B.

A chromatographic analysis of the endopolygalacturonase (endoPG) enzyme produced by the fungus responsible for the foliar symptoms of the silver-leaf disease was performed on these samples (Senda et al., 2001).

The total number of samples that were analyzed corresponds to 24 per species, considering 3 biological replicates (pertaining to 3 different plant leaves) and 2 technical replicates (grinding supernatant of the same biological replicate). The analysis was performed using the ELISA technique, where leaves were subjected to grinding and crushing on buffer, then were incubated with primary and secondary antibody, to then determine the OD at a 450 nm wavelength to determine endoPG concentration (having already performed a calibration curve using synthetic peptides).

On the other hand, nursery plans were used as control, which were inoculated with virulent strains of the pathogen, checking presence of the pathogen by isolating in culture media and detecting with PCR, just as was checked on plants naturally inoculated with the pathogen. The antibody was able to detect the enzyme in each one of the cases, excepting kiwi, that underwent some modification on its detection protocol. Plants were considered to be sick if showed at least twice the endoPG concentration (Herrera et al., 1995), in respect to the average value of 10 negative controls. Treatments that were used and detected concentrations are presented next (Table 5):

TABLE 5

Treatments used to verify differences on endoPG concentration present
in plants with different silver leaf symptom intensities.

| Treatment | Sample | EndoPG concentration/gpf | Symptomatology |
|---|---|---|---|
| 1 | 48 | 0.0007317 | Symptomatic |
| 2 | 25 | 0.0005834 | Symptomatic |
| 3 | 73 | 0.0005421 | Symptomatic |
| 4 | 41 | 0.0005369 | Asymptomatic |
| 5 | 40 | 0.0004867 | Asymptomatic |
| 6 | 15 | 0.0004187 | Asymptomatic |
| 7 | 37 | 0.0004122 | Asymptomatic |
| 8 | 3 | 0.0004024 | Asymptomatic |

TABLE 5-continued

Treatments used to verify differences on endoPG concentration present
in plants with different silver leaf symptom intensities.

| Treatment | Sample | EndoPG concentration/gpf | Symptomatology |
|---|---|---|---|
| 9 | 39 | 0.0004019 | Asymptomatic |
| 10 | 17 | 0.0003668 | Asymptomatic |
| 11 | 36 | 0.0003623 | Asymptomatic |
| 12 | 18 | 0.0003614 | Asymptomatic |
| 14 | 38 | 0.0000974 | Asymptomatic |
| 15 | 100 | 0.0000754 | Asymptomatic |
| 16 | 99 | 0.0000701 | Asymptomatic |
| 17 | C2 | 0.0001477 | Healthy control |
| 18 | C2 | 0.0001406 | Healthy control |

Results show that, for plum, cherry, peach and blueberry, minimum detection levels in asymptomatic plants were considerably higher than twice the control values. For apple, on the other hand, was considerably higher in each case, but in some of them, no superior than twice the control values.

Example 3: Kit Preparation for Early Detection of Silver Leaf in Fruit Orchards: Functionalized Nanoparticle Sensibility Determination in Reactive Strips To determine if the nanoparticles are capable of detecting endoPG, an evaluation assay was performed in nitrocellulose membrane strips with nanoparticles on them, where one of their ends was submerged in the grinding supernatant of apple foliar samples from plants infected with the pathogen. The supernatant moved along the nitrocellulose strip by capillary diffusion unto the nanoparticles, showing a circumference on the strips where the latter were added.

Conjugate specificity was determined by means of the interaction of enzyme preparations that show endoPG1-like functions with it, using an in-solution colorimetric assay. The assay was performed by testing two commercial enzymatic preparations solutions composed by a mixture of enzymes, corresponding to the Natuzym DP Ultra product, comprised of pectolyase, polygalacturonase, pectinesterase and arbanase, and DeltaZym VR AC-100 with cellulases and hemicellulases. Both enzymatic preparations were in a 1:10 and 1:100 ratio with water and PBS buffer respectively. The reaction was performed by adding 6 mL of the enzymatic complex to 200 µL of nanoparticles. Results of this assay showed that no color change occurred in any of the reactions in respect to the 1:10 control. An UV-VIS spectrophotometric analysis delivered curves for each of the different reactions and it showed that they followed the same absorbance pattern, indicating that the antibody did not recognize any of those enzymes.

Example 4: Immunoassay Kit and Evaluation of its Detection

The immunoassay kit was prototyped based on the Tucker et al., 1980; Nogata et al., 1993; Priya et al., 199, and Srivastava y Dwivedi, 2000, studies.

The immunoassay kit is comprised by a nitrocellullose membrane reactive strip composed by four areas or zones, which correspond to the sample pad, the test zone, the control zone and an absorption pad placement (FIG. 7, panel A). The nanoparticle complex is applied on the lower part of the membrane. The test zone and control zone both contain primary and secondary antibodies and then the adsorption pad is placed.

The detection is based on the diffusion of conjugated gold nanoparticles through the nitrocellulose membrane, that by means of capillary diffusion move towards specific adsorption sites for enzyme detection by primary and secondary antibodies that are immobilized onto it. The reaction used a synthetic endoPG1, which reacted with the lines that contained NpsAu+Lc+Ab complex on the nitrocellulose strip and with the control line. Protocols were optimized for a reaction time of 15 to 20 minutes (FIG. 7, panel B). Specifically, proper functioning of the kit comprises diffusion of the NPsAu where the NpsAu+Lc+Ab complex is rehydrated and is mixed with the sample. When the sample contains endoPG, the enzyme is captured by the antibody and this new complex diffuses towards the "test" area, where its retained by the membrane immobilized anti-endoPG antibody, detectable by a red colored line. Anti-endoPG/Np complex excess that surpasses the "test" area keeps on diffusing to the control area where it reacts with the anti-rabbit IgG secondary antibody, developing a red color ("control"), validating the method of detection (FIG. 7, panel A). If a red color appears on both the control and test zones the sample is considered to be positive. If the kit does not detect endoPG on the sample, only one red colored area will appear in the control zone, because immobilization of the anti endoPG antibody/Nps complex does not occur due to absence of the antigen (FIG. 7, panel D).

Example 5: Kit Concept Test in 6 Fruit Orchards of Economic Interest

To start the kit concept test an enzymatic extract was prepared and added to the nitrocellulose membrane that has the immobilized antibodies. This extract was prepared by weighing 1 g of sample and cutting in small pieces by hand. Then, it was macerated with 3 mL of 1×PBS, the mash was retained and then washed with acetone. Remaining residue was resuspended in 1×PBS buffer and stirred. Finally, the pellet was discarded and the supernatant was retained, the last one corresponding to the enzymatic extract that reacts with the components on the reactive strip.

The prototype was validated in the laboratory using blueberry samples from. Vilcún, and apple tree samples from Chillán, naturally infected with *C. purpureum*, and also artificially inoculated plants with virulent strains of the fungus. For the negative control, in vitro plant leaves were used.

In both species an approximate reaction time of 20 min was observed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

BIBLIOGRAPHY

INIA, Instituto de investigaciones agropecuarias. (2018). Investigadores INIA presentaron investigación en plateado de los frutales en Congreso de Fitopatología en EEUU. https://www.inia.cl/blog/2018/09/13/investigadores-inia-presentaron-investigacion-en-plateado-de-los-frutales-en-congreso-de-fitopatologia-en-eeuu/

INIA. (2006). Revista Tierra Adentro: frutales y viñas. http://biblioteca.inia.cl/medios/biblioteca/ta/NR33449.pdf P. Preechakasedkit et al.,/Biosensors and Bioelectronics (2012) 562-566.

Portal frutícola (2019). Enfermedad del plateado en carozos y ardádanos. https://www.portalfruticola.com/noticias/2019/08/07/enfermedad-del-plateado-en-carozos-y-arandanos/30

Rojo C, Becerra V, France A, Paredes M, Buddie A, alzarini M. (2017). Genetic diversity of *Chondrostereum purpureum* (Pers.) Pouzar causing silverleaf disease on blueberries in Chile. Gayana Bot. 74(1): 176-188.

France, A., Grinbergs, D. & Carrasco, J. (2016). First detection of silverleaf (*Chondrostereum purpureum*) on rabbiteye blueberry (*Vaccinium virgatum*) and disease damages. XI International *Vaccinium* Symposium 1180.

Grinbergs, Daina & Chilian, J. & Lisboa, K. & France, Andres. (2019). First Report of Silverleaf Disease Caused by *Chondrostereum purpureum* on Murta (Ugni molinae) in Chile. Plant Disease. 103. 2140-2140. 10.1094/PDIS-12-1bakan, 8-2285-PDN.

Grinbergs, D.; Chilian, J.; Carrasco-Fernandez, J.; France, A.; Moya-Elizondo, E.; Gerding, M. A PCR-based method for the rapid detection of *Chondrostereum purpureum* in apple. Plant Dis. 104, 71, 702-707.

Grinbergs, D.; Chilian, J.; Hahn, C.; Reyes, M.; Isla, M.; France, A.; Börve, J. Silverleaf (*Chondrostereum purpureum*) Effects on Japanese Plum (*Prunus salicina*). Preprints.org 2021, 2021060160. https://doi.org/10.20944/preprints202106.0160.v1

The invention claimed is:

1. An antibody to detect presence of *Chondrostereum purpureum* fungus in a plant sample, wherein the antibody has a heavy chain defined by the amino acid sequence SEQ ID No. 2 and a light chain defined by the amino acid sequence SEQ ID No. 4, and wherein said antibody is conjugated with gold nanoparticles through an L-cysteine residue to form gold nanoparticles+L-cysteine+specific anti-endoPG monoclonal antibody complex (NpsAu+Lc+Ab complex) and specifically binds to enzyme endopolygalacturonase from *Chondrostereum purpureum* (anti-endoPG antibody), wherein the gold nanoparticles have an average diameter of 25 nm and a surface charge of ~19.9 mV.

2. A method for detecting the *Chondrostereum purpureum* fungus presence in a plant tissue sample comprising the steps of:

a. preparing the vegetable or tree tissue sample of interest to obtain a supernatant from the sample, b. establishing contact between the supernatants of the sample to be analyzed with the antibody of claim 1, and c. evaluating the specific union of the anti-endoPG antibody, where the sample contains the fungus if the antibody is specifically bound to the sample.

3. The method for detecting the *Chondrostereum purpureum* fungus presence in a plant tissue sample in accordance with claim 2, wherein, to prepare the sample, 1 g of plant tissue is grinded and crushed, left to macerate, and washed with an organic solvent and the supernatant of the sample is retained.

4. The method for detecting the *Chondrostereum purpureum* fungus presence in a plant tissue sample in accordance with claim 2, wherein the plant tissue corresponds to leaves, wood, roots, seeds.

5. The method for detecting the *Chondrostereum purpureum* fungus presence in a plant tissue sample in accordance with claim 2, wherein the specific union of the anti-EndoPG antibody is evaluated using a method selected from the group that consists on a lateral flow immunochromatography or ELISA procedure.

6. A kit for the fast detection of the *Chondrostereum purpureum* fungus in a plant sample comprising:

a reactive strip composed of a nitrocellulose membrane where there are differentiated areas for the sample pad, test zone, control zone and absorption pad, where the test and control zone have the NpsAu+Lc+Ab complex with antibody of claim 1;

detection secondary antibodies; and instructions of use.

7. The kit for the quick detection of the *Chondrostereum purpureum* fungus in a plant sample in accordance with claim 6, wherein the detection secondary antibodies are anti-rabbit IgG.

8. The kit for the quick detection of the *Chondrostereum purpureum* fungus in a plant tissue sample in accordance with claim 7, wherein the sample to be evaluated is a supernatant of a processed plant sample.

9. The kit for the quick detection of the *Chondrostereum purpureum* fungus presence in a plant tissue sample in accordance with claim 8, wherein the sample to be evaluated is prepared by grinding and/or crushing plant tissue, then left to macerate, washed with an organic solvent, and the supernatant of this sample is retained.

10. The kit for the quick detection of the *Chondrostereum purpureum* fungus of claim 9, wherein the plant tissue is leaves, wood, roots and/or seeds.

\* \* \* \* \*